United States Patent

Solovay

[19]

[11] Patent Number: 5,948,191
[45] Date of Patent: Sep. 7, 1999

[54] LOW PROFILE, THERMALLY SET WRAPPED COVER FOR A PERCUTANEOUSLY DEPLOYED STENT

[75] Inventor: Kenneth S. Solovay, Fort Lauderdale, Fla.

[73] Assignee: Cordis Corporation, Fort Lauderdale, Fla.

[21] Appl. No.: 08/946,519

[22] Filed: Oct. 7, 1997

Related U.S. Application Data

[62] Division of application No. 08/680,435, Jul. 15, 1996, Pat. No. 5,741,326.

[51] Int. Cl.⁶ .......................... B32B 31/00; A61M 29/00; A61F 2/06; A61F 2/02
[52] U.S. Cl. .......................... 156/86; 156/247; 606/192; 606/194; 606/195; 623/1; 623/11; 623/12
[58] Field of Search .............. 53/429, 430, 441, 53/442; 156/86, 247; 623/1, 11, 12; 606/192, 194, 195

[56] References Cited

U.S. PATENT DOCUMENTS

| | | | |
|---|---|---|---|
| 4,878,906 | 11/1989 | Lindemann et al. | 623/1 |
| 5,019,090 | 5/1991 | Pinchuk | 606/194 |
| 5,123,917 | 6/1992 | Lee | 623/1 |
| 5,135,536 | 8/1992 | Hillstead | 606/195 |
| 5,163,951 | 11/1992 | Pinchuk et al. | 623/1 |
| 5,282,824 | 2/1994 | Gianturco | 606/198 |
| 5,330,500 | 7/1994 | Song | 606/198 |
| 5,476,506 | 12/1995 | Lunn | 623/1 |
| 5,562,725 | 10/1996 | Schmitt et al. | 623/1 |
| 5,693,066 | 12/1997 | Rupp et al. | 606/198 |
| 5,811,043 | 9/1998 | Horrigan et al. | 264/138 |

FOREIGN PATENT DOCUMENTS 0603959  6/1994  European Pat. Off. .

OTHER PUBLICATIONS

Product specification brochure for heat shrink tubing published by Advanced Polymer Incorporated, publication date unknown (one page). To the best of applicant's knowledge, this publication was published prior to Jul. 15, 1995 (one year to the filing date of the instant application).

*Biocompatability of Clinical Implant Materials,* vol. II, Chapter 8, pp. 178–205, 1981, CRC Series in Biocompatability, David F. Williams, Editor, CRC Press, Inc., Boca Raton, Florida, publication date unknown (thirty–two pages). To the best of applicant's knowledge, this publication was published prior to Jul. 15, 1995 (one year prior to the filing date of the instant application).

Instruction pamphlet for Cordis Sheath Introducer System published by Cordis Corporation, May 1994 (twenty four pages).

C.T. Doter, *Investigative Radiology,* 9:329–332 (1969).

*Primary Examiner*—David A. Simmons
*Assistant Examiner*—J. A. Lorengo
*Attorney, Agent, or Firm*—Watts, Hoffman, Fisher & Heinke

[57] ABSTRACT

An endoprosthesis assembly for percutaneous deployment on a balloon catheter is disclosed. The assembly includes a radially expandable stent overlied by a tubular, low profile stent cover wrapped over the stent. The wrapped cover is thermally set to maintain its low profile wrapped configuration during deployment of the assembly. At the treatment site, the balloon portion of the catheter is inflated causing the stent to expand radially and the stent cover to unwrap and open to conform to the expanded configuration of the stent.

6 Claims, 4 Drawing Sheets

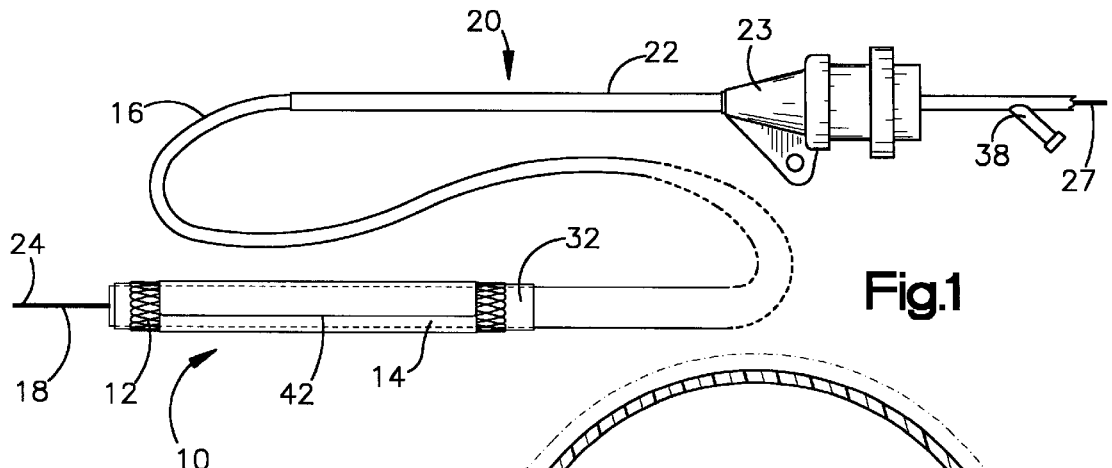
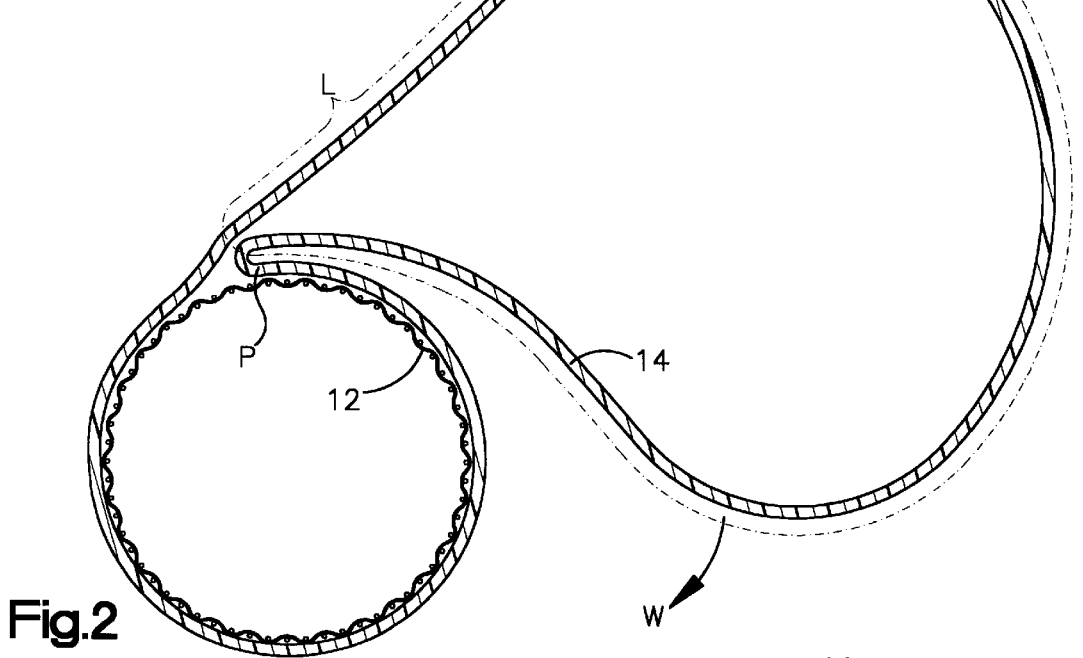
Fig.1
Fig.2
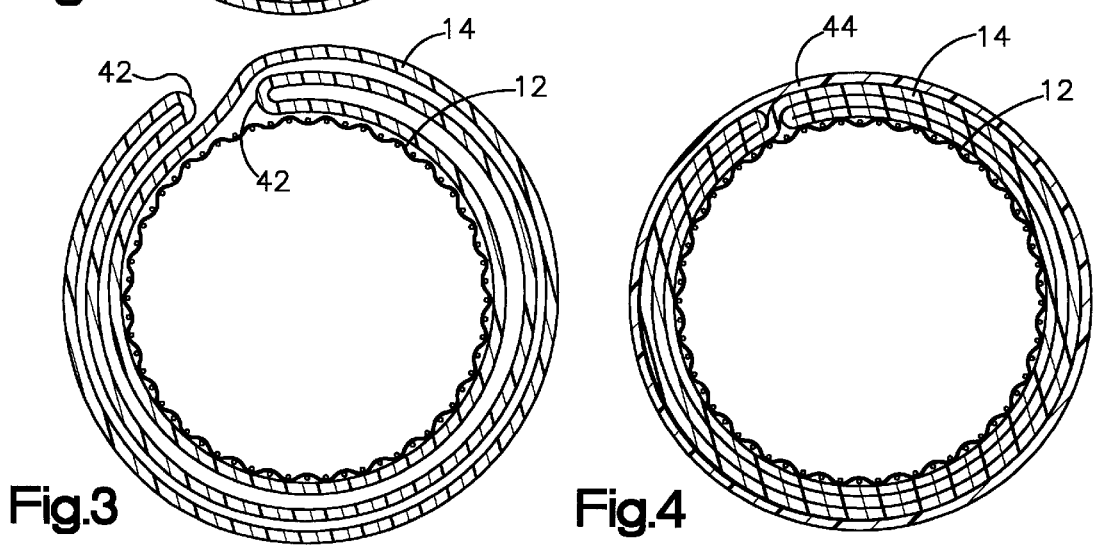
Fig.3
Fig.4

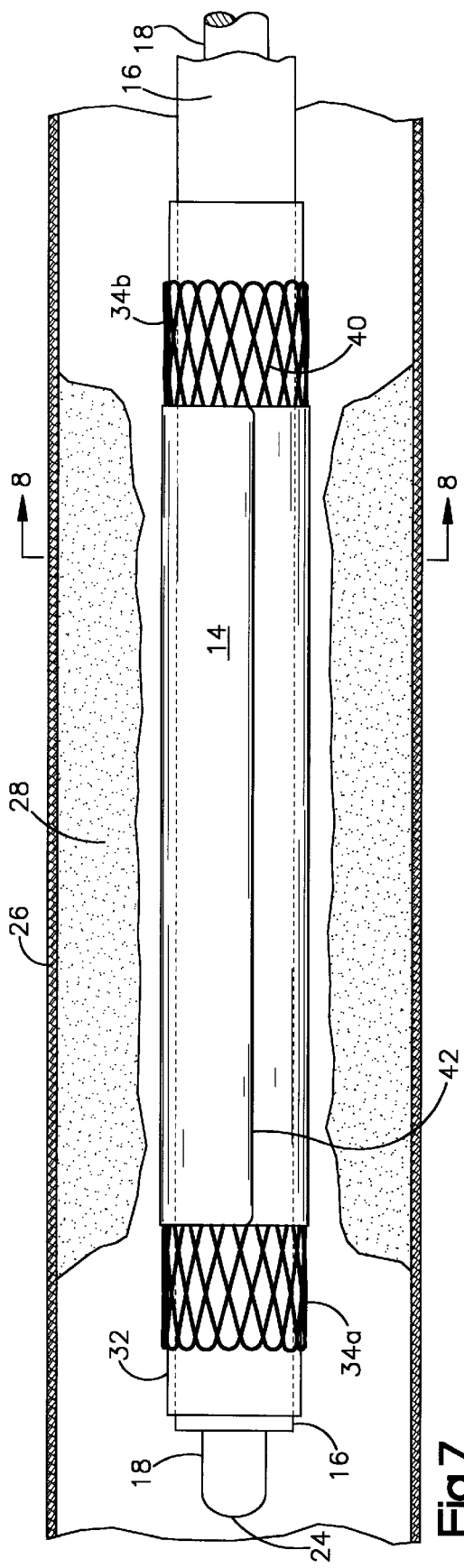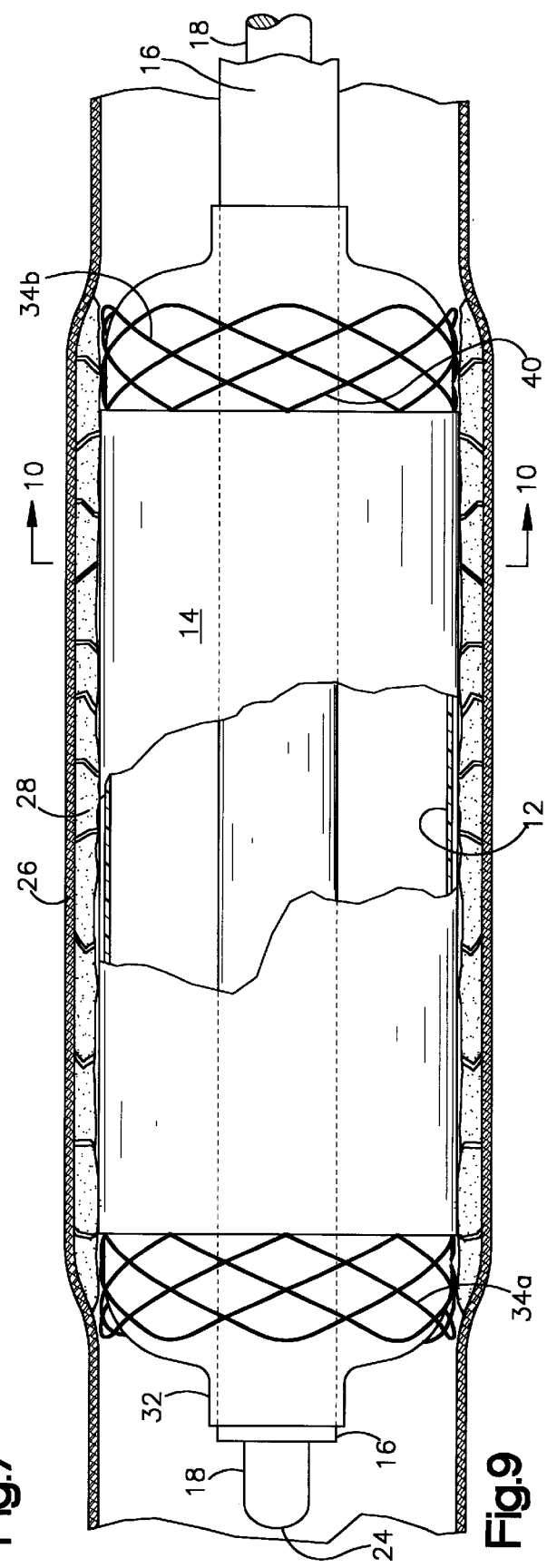

5,948,191

LOW PROFILE, THERMALLY SET WRAPPED COVER FOR A PERCUTANEOUSLY DEPLOYED STENT

This is a divisional of application Ser. No. 08/680,435 filed on Jul. 15, 1996 now U.S. Pat. No. 5,741,326.

FIELD OF THE INVENTION

This invention generally relates to an endoprosthesis assembly including a wrapped cover for a percutaneously deployed stent and a method for making such an endoprosthesis assembly, and, more particularly, the invention relates to a tubular shaped, woven polyester cover wrapped around an outer periphery of a stent and thermally set to maintain a low profile configuration during percutaneous deployment of the endoprosthesis assembly to a treatment site.

BACKGROUND OF THE INVENTION

Various endoprostheses assemblies which include expandable stents have been proposed or developed for use in association with angioplasty treatments and other medical procedures. The endoprosthesis assembly is percutaneously routed to a treatment site and the stent is expanded to maintain or restore the patency of a body passageway such as a blood vessel. A stent is typically cylindrical in shape comprising an expandable, open frame which radially expands upon exertion of an outwardly directed radial force on an inner surface of the stent frame.

Stents for endovascular implantation into a blood vessel, artery or the like to maintain or restore the patency of the passageway have been deployed percutaneously to minimize the invasiveness associated with surgical exposure of the treatment site. Percutaneous deployment is initiated by an incision into the vascular system of the patient, typically into the femoral artery. A tubular or sheath portion of an introducer is inserted through the incision and extends into the artery. The introducer has a central lumen which provides a passageway through the patient's skin and artery wall into the interior of the artery. An outwardly tapered hub portion of the introducer remains outside the patient's body to prevent blood from leaking out of the artery along the outside of the sheath. The introducer lumen includes a valve to block blood flow out of the artery through the introducer passageway. A distal end of a guide wire is passed through the introducer passageway into the patient's vasculature. The guide wire is threaded through the vasculature until the inserted distal end extends just beyond the treatment site. The proximal end of the guide wire extends outside the introducer.

For endovascular deployment, a stent, in an unexpanded or constricted configuration is crimped onto a deflated balloon portion of a balloon catheter. The balloon portion is normally disposed near a distal end of the balloon catheter. The catheter has a central lumen extending its entire length. The distal end of the balloon catheter is threaded onto the proximal end of the guide wire. The distal end of the catheter is inserted into the introducer lumen and the catheter is pushed along the guide wire until the stent reaches the treatment site. At the treatment site, the balloon is inflated causing the stent to radially expand and assume an expanded configuration. When the stent is used to reinforce a portion of the blood vessel wall, the stent is expanded such that its outer diameter is approximately 10% to 20% larger than the inner diameter of the blood vessel at the treatment site, effectively causing an interference fit between the stent and the blood vessel that inhibits migration of the stent. The balloon is deflated and the balloon catheter is withdrawn from the patient's body. The guide wire is similarly removed. Finally, the introducer is removed from the artery.

The introducer provides a passageway from the external environment into the patient's vascular system. The size of the cross sectional area of the introducer sheath portion determines the required size of the entrance incision or wound into the vascular system. Reduction in the required size of the introducer passageway, which is typically measured in terms of "French size," permits an introducer with a smaller outer diameter to be used and results in a correspondingly smaller entrance incision into the patient's vascular system. A smaller entrance incision reduces the probability that surgical closure of the wound will be necessary and reduces the risk of developing hematomas and other bleeding complications. However, efforts to reduce the required size of the introducer passageway are limited by the deployment cross sectional profile of the endoprosthesis assembly as mounted on the balloon portion of the catheter.

Typically, a stent consists of two or more struts or support members connected together into a radially expandable frame. The struts define open or void areas upon expansion of the stent from the constricted configuration to an expanded configuration at the treatment site. Larger void areas can permit malignant tissue growth through the stent openings into the body passageway and can also allow undesired contact between blood in the blood vessel and damaged portions of the vessel wall. Stent covers have been proposed to alleviate the problems associated with stent openings. Unfortunately, conventional stent covers greatly increase the cross sectional profile of the endoprosthesis assembly, necessitating the use of a larger sized introducer and requiring a correspondingly larger entrance incision.

Further, as disclosed in co-pending application Ser. No. _____, filed Jun. 27, 1996, and entitled Controlled Porosity Endovascular Implant (Atty. Docket No. 13-949), assigned to the assignee of the present invention and is incorporated herein by in its entirety by reference, while the stent cover functions to prevent malignant tissue growth through the stent openings, some porosity in the stent cover is desirable. The stent cover should have pores of sufficient size to allow cellular ingrowth and capillary formation but small enough to prevent intrusions into the stent passageway as discussed above.

One proposed prior art stent cover comprises a tubular sleeve designed to be mechanically deformed around a constricted stent by folding or bending the sleeve into a layered or bunched configuration overlying the stent. The sleeve is affixed to the stent by stitching or gluing. The resulting configuration is characterized by an uneven, bulky profile for the endoprosthesis assembly. Such a configuration compromises easy insertion of the endoprosthesis assembly through the introducer passageway and necessitates a larger diameter passageway.

Other proposed stent cover designs require the use of a deployment sheath to maintain the stent cover in a collapsed configuration about the stent during insertion and deployment. When the stent is at the treatment site, the deployment sheath is withdrawn prior to inflation of the balloon. A problem with using a deployment sheath is that it increases the deployment cross sectional profile of the assembly, which, as explained above, requires use of a larger French size introducer.

There remains a need for an endoprosthesis assembly including a stent cover that does not significantly increase the deployment cross sectional profile of the assembly.

There further remains a need for an endoprosthesis assembly including a stent cover wherein the assembly can be percutaneously deployed without the necessity of a deployment sheath to maintain the cover in a wrapped configuration about the stent during deployment of the assembly. Also, there remains a need for an endoprosthesis assembly including a stent cover that prevents undesirable tissue growth through the stent openings yet provides sufficient porosity for desirably cellular ingrowth and capillary formation. Finally, there remains a need for an endoprosthesis assembly stent covering providing the above advantages and that can be used with existing stents.

SUMMARY OF THE INVENTION

The present invention provides an endoprosthesis assembly for percutaneous deployment and implantation within a body passageway. The endoprosthesis assembly includes a stent and a stent cover. The assembly is affixed to a balloon portion of a balloon catheter for deployment to a treatment site within a patient's vasculature.

The stent comprises a radially expandable cylindrical frame while the stent cover comprises a thin walled, single layer polyester woven sleeve having a length just less than a length of the stent. The inner diameter of the cover is matched to the desired, expanded outer diameter of the stent. Normally, a The stent cover is wrapped around the stent when the stent is in an unexpanded constricted configuration and is thermally set in the wrapped configuration. After being thermally set, an outer surface of the wrapped cover has a uniform and smooth cylindrical shape. The thermally set cover remains in the wrapped configuration during deployment of the endoprosthesis assembly to the treatment area.

The unwrapped diameter of the stent cover and the expanded diameter of the stent must be matched to the size of the blood vessel that is to be treated. As the balloon of the balloon catheter is expanded, the stent expands and stent cover correspondingly unwraps. The stent is expanded until it is fully seated compressing the unwrapped cover against the blood vessel intraluminal wall.

The stent cover remedies the problems associated with the open spaces of the stent frame, while its uniform cylindrical shape after thermal setting minimizes the increase in the assembly's outer diameter due to the cover. The outward radial force necessary to unwrap the cover is less than the radial force necessary to expand the stent. Further, once the cover is unwrapped or open, it does not have a tendency to return to its wrapped configuration and therefore does not tend to apply an inwardly directed radial force on the expanded stent which could cause the stent to collapse.

The cross sectional profile of the endoprosthesis assembly of the present invention allows a significantly smaller introducer passageway to be used than was previously possible using traditional stent covers. Further, the uniformity in the outer surface of the wrapped cover eliminates the need for a deployment sheath and the attendant increase in cross section of the assembly such a sheath would cause.

To fabricate the endoprosthesis assembly of the present invention, polyester fiber is woven into a tubular shaped sleeve. Preferably, the sleeve is comprised of a single ply polyester material having a thickness of approximately 0.004 inches. The preferred polyester is polyethylene terephthalate (PET). The cover is cut from the woven sleeve. The cover is cut to a length just slightly less than a length of the selected stent the cover will be used with. The inner diameter of the cover is selected to match the outer diameter of the stent when the stent is expanded to a desired diameter within a blood vessel.

The stent cover is affixed to the stent with a single tied stitch extending through the cover and looped around a support member of the stent frame. The cover is then wrapped tightly around the stent while the stent is in its unexpanded configuration.

The stent and wrapped cover are inserted into a piece of heat shrink tubing. The tubing is sized to fit snugly over the cover. Then the endoprosthesis assembly is exposed to an elevated temperature causing the heat shrink tubing to shrink and radially compress the cover. The heat and the heat shrink tubing set the cover in its wrapped configuration. The heat shrink tubing is then peeled off. The stent is positioned on the balloon portion of a balloon catheter and the stent is crimped onto the catheter balloon portion.

During deployment, the stent cover remains in its thermally set, wrapped configuration until during implantation the inner surface of the cover overlying the stent is subjected to the outwardly directed radial force extended by the expanding stent. A stent cover fabricated of woven PET polyester exhibits the advantages of so-called non-compliant stents, namely, good long term fatigue resistance to pulsatile pressure, resistance to aneurysms and leaks and good healing characteristics.

These and other advantages and features of this invention will be clearly understood through consideration of the following detailed description of the invention in conjunction with the accompanying drawings.

BRIEF DESCRIPTION OF THE DRAWINGS

FIG. 1 is a side elevation view of an endoprosthesis assembly of the present invention and a delivery assembly including a balloon catheter for percutaneous deployment of the endoprosthesis assembly;

FIG. 2 is a cross section view of the endoprosthesis assembly of FIG. 1 including a stent and a stent cover partially wrapped around the stent;

FIG. 3 is a cross section view of the endoprosthesis assembly of FIG. 1 with the stent cover completely wrapped around the stent;

FIG. 4 is a cross section view of the endoprosthesis assembly of FIG. 1 with a section of heat shrink tubing overlying the stent cover;

FIG. 7 is a side elevation view of the endoprosthesis assembly of FIG. 1 mounted on the balloon catheter and positioned within a partially occluded portion of a blood vessel;

FIG. 9 is a side elevation view of the endoprosthesis assembly of FIG. 1 mounted on the balloon catheter with a balloon portion of the catheter inflated expanding the stent, unwrapping stent cover and increasing a size of the opening through the blood vessel.

DESCRIPTION OF THE PREFERRED EMBODIMENT

I. Configuration and Use of the Endoprosthesis Assembly

Figure 10:
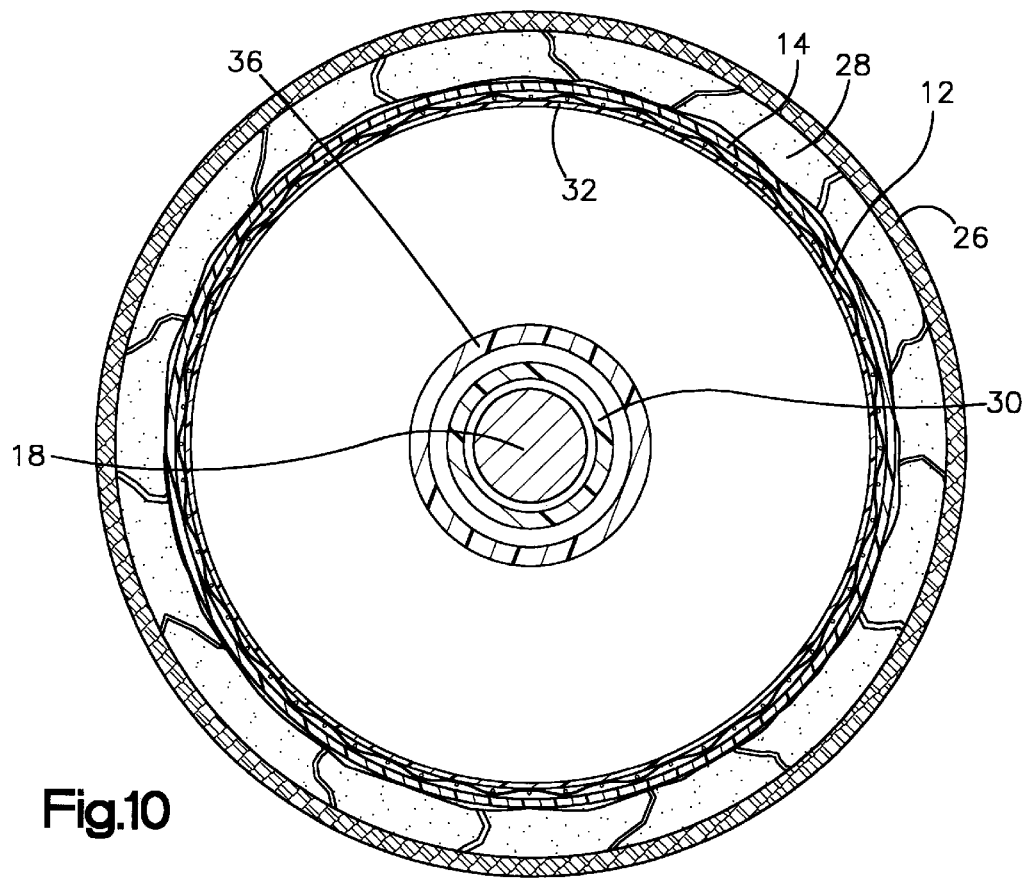
FIG. 10 is a cross section view of the endoprosthesis assembly and the balloon catheter as seen from a plane indicated by the line 10—10 in FIG. 9.

Turning to the drawings, the present invention provides for an endoprosthesis assembly 10 including a stent 12 and a stent cover 14 wrapped around an outer surface of the stent. The stent 12 is cylindrical with an open center passageway and is radially expandable between an unexpanded or constricted configuration (FIGS. 1 and 5–8) and an expanded configuration (FIGS. 9 and 10). The stent cover 14 is in a wrapped configuration when the stent is in its unexpanded configuration and unwraps to an open or unwrapped configuration when the stent 12 is in its expanded configuration.

Figure 5:
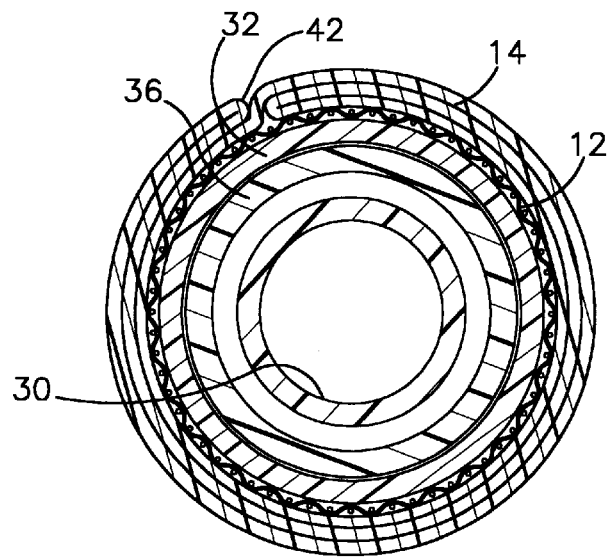
FIG. 5 is a cross section view of the endoprosthesis assembly of FIG. 1 mounted on the balloon catheter with the stent cover thermally set in its wrapped configuration and the section of heat shrink tubing stripped off.
Figure 6:
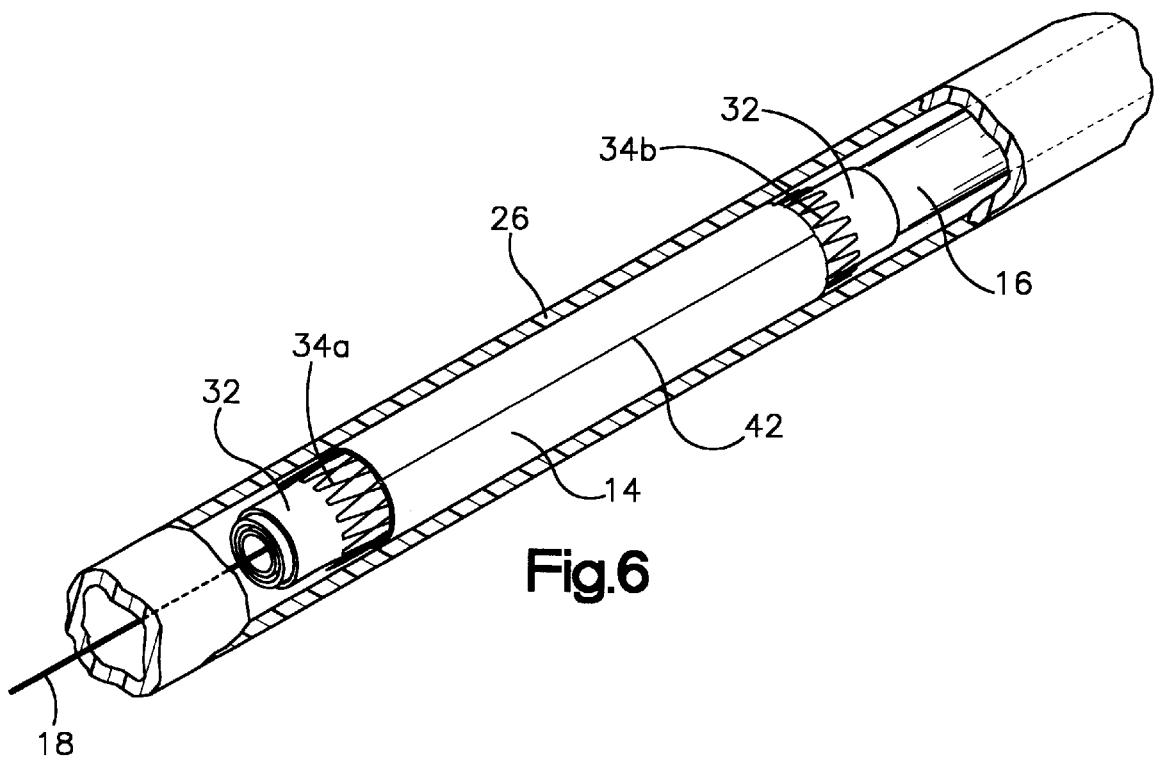
FIG. 6 is a perspective view of the endoprosthesis assembly of FIG. 1 mounted on the balloon catheter within a patient's blood vessel.
Figure 8:
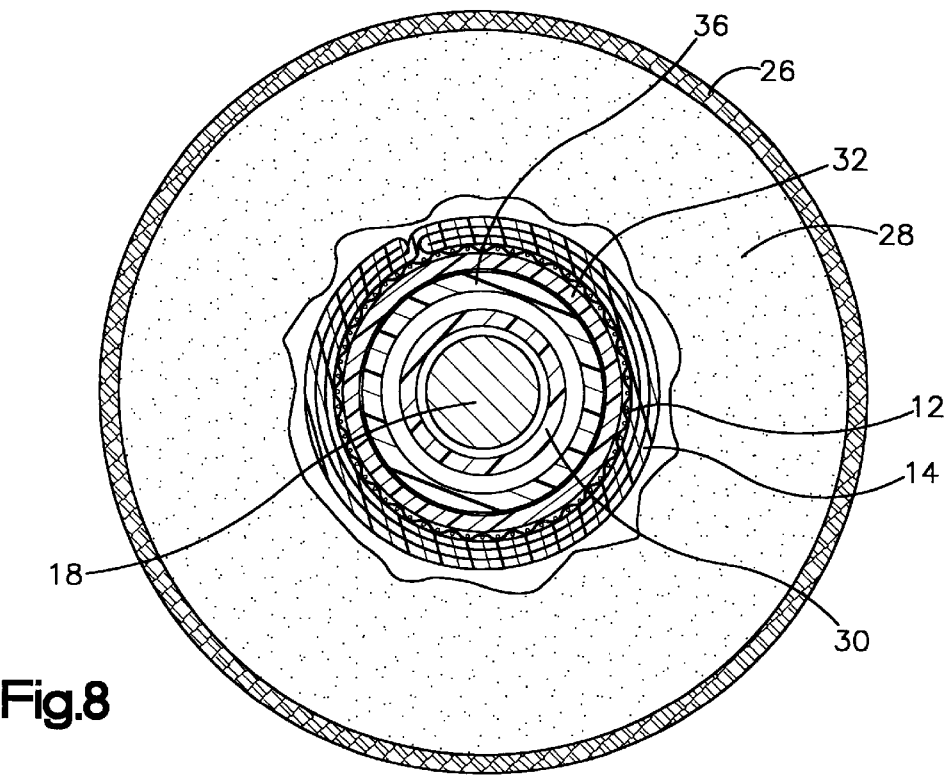
FIG. 8 is a cross section view of the endoprosthesis assembly and the balloon catheter as seen from a plane indicated by the line 8—8 in FIG. 7.

The assembly 10 is percutaneously deployed and implanted within a body passageway using a delivery assembly, best seen in FIGS. 1 and 6, including a percutaneous transluminal angioplasty balloon catheter 16, a guide wire 18 and a catheter introducer 20. A tubular distal portion or sheath 22 extends from a tapered hub 23 of the introducer 20. The sheath 22 is inserted through an incision and extends into an artery of a patient such that the hub 23 is pressed against the skin surrounding the incision. The hub 23 is pressed against the incision to prevent blood leakage from the artery around an outer periphery of the sheath 22.

A cylindrical interior passageway (not shown) extends the length of the introducer 20. The diameter of the passageway is normally designated as the "French size" of the introducer 20. A French size is equivalent to approximately 0.0131 inches (0.33 mm.). Thus, a French size of eight corresponds to a passageway diameter of approximately 0.105 inches (2.67 mm.). A one way valve is disposed in the introducer passageway to prevent blood from leaking out of the artery prior to insertion of the catheter 16 into the introducer passageway.

A distal end 24 of the guide wire 18 is threaded through the introducer passageway and is advanced through the patient's vasculature to a position just beyond a treatment site or region (FIGS. 7–10). A proximal end 27 of the guide wire 18 remains outside the patient'ss body. The treatment site represented in FIGS. 7–10 is a portion of a blood vessel 26 that is partially occluded by plaque material 28 adhering to the inner or intraluminal wall of the blood vessel. It should also be appreciated, however, that the assembly 10 of the present invention could be advantageously employed for other endovascular uses such as; reinforcing a damaged portion of a blood vessel; treating aneurysms, arteriorvenous fistulas, stenosis, occlusive disease, miliary strictures, malignant tumors in esophagous; and other uses known to those skilled in the art.

The balloon catheter 16 includes a central lumen defined by an inner wall 30. The catheter 20 includes a flexible walled, inflatable balloon portion 32 near a distal end of the catheter. The stent 12, in its unexpanded configuration, is crimped to the balloon portion 32 using a conventional crimping tool (not shown) to secure the endoprosthesis assembly 10 to the catheter 20 during percutaneous deployment of the assembly. With the guide wire 18 held stationary, the distal end of the catheter is slid over the proximal end 27 of the guide wire 18, such that the guide wire extends into and through the catheter central lumen. The catheter 16 is advanced along the stationary guide wire 18 until the endoprosthesis assembly 10 is positioned at the blood vessel treatment site.

Fluid is injected into a cylindrical channel of the catheter 16 defined by the inner wall 30 and an outer wall 36 (FIGS. 5, 8 and 10) via a Y-port connector 36 located near a proximal end of the catheter 16. The catheter outer wall 36 includes an aperture (not shown) in the region of the balloon portion permitting fluid to flow into and out of the balloon portion 32. Injection of the fluid through the Y-port connector 36 and into the cylindrical channel causes the balloon portion 32 to expand outwardly from the catheter outer wall 36 as shown in FIGS. 9 and 10.

The expansion of the balloon portion 32 exerts an outwardly directed radial pressure on the stent 12 and the overlying wrapped stent cover 14. The radial pressure is sufficient to cause the stent 12 to expand radially outwardly and the cover 14 to unwrap and open radially outwardly. The radial force required to open the stent cover 14 is less than the radial force necessary to expand the stent 12. The expanding stent 12 and unwrapping stent cover 14 compress the occluded material 28 against the blood vessel intraluminal wall thereby enlarging the size of the opening through the blood vessel 26. The balloon portion 32 is expanded to a diameter such that the stent 12 is firmly secured at the treatment site by an interference fit with the occluded material and/or the blood vessel intraluminal wall. If no occluded material 28 were present in the blood vessel 26, the outer diameter of the stent 12 would be expanded to a diameter slightly larger than the relaxed inner diameter of the blood vessel. This would result in an interference fit between the assembly 10 and the blood vessel 26 thereby preventing migration of the assembly from the treatment site over time.

After the stent 12 has been expanded to a proper diameter, the fluid injected between the catheter inner and outer walls 30, 36 is pumped out through the Y-port connector 38 deflating the balloon portion 32. The stent 12 has sufficient hoop strength to maintain its expanded configuration when the balloon portion 32 is deflated. "Hoop strength" as used herein refers to the intraluminal force exerted by the expanded stent 12. This force is measured by expanding a stent within a latex tube (not shown). The pressure surrounding the exterior of the tube is gradually increased until the expanded stent collapses. The pressure at collapse is denominated the "hoop strength" of the stent. It is generally appreciated by those skilled in the art that hoop strength is a function of the amount of expansion undergone by the stent. The stent 12 of the present invention preferably is a variably expanding stent, that is, the stent may be expanded to any outer diameter within a range of outer diameters. Once expanded to a desired outer diameter, the stent 12 will remain in that expanded configuration. For example, the stent 12 may be capable of expanding to any desired outer diameter between 0.157 in. and 0.276 in. (4 mm. and 7 mm.). Corresponding to the range of outer diameters, the stent 12 has a corresponding range of hoop strengths. Typically, hoop strength and expanded stent diameter are inversely proportional.

As will be explained below, the stent cover 14 is fabricated such that an inner diameter of the stent cover is at least as large as an outer diameter of the stent 12 in its desired expanded configuration. That is, if it is desired to expand the stent 12 to an outer diameter of 0.197 in. (5.0 mm.), the stent cover 14 will be fabricated to have an inner diameter of at least 0.197 in. (5.0 mm.). Moreover, the cover 14 is fabricated of a woven polyester material that, once opened or released from its wrapped configuration, does not tend to revert to the wrapped configuration after the assembly 10 has been implanted endovascularly in the blood vessel 26.

Thus, the cover 14 does not apply any significant inwardly directed radial force that would tend to collapse the expanded stent 12.

After implantation of the assembly 10, the catheter 16 is removed by sliding it in a proximal direction until the distal end of the catheter clears the proximal end 27 of the guide wire 18. Then the guide wire 18 is withdrawn in the same manner until the guide wire distal end 24 clears the introducer hub 23. Finally, the introducer sheath 22 is withdrawn from the patient.

II. Components and Assembly

The stent 12 has an open frame structure comprised of struts or support members 40 joined to enable the frame to radially expand and collapse. As can best be seen in FIGS. 7 and 9, the support members 40 define void spaces that increase in size as the stent expands. The support members 40 form a generally cylindrical shaped frame having a longitudinal axis. Preferably, the support members 40 consist of sinusoidally shaped tantalum wires having a diameter of 0.0075 inches (0.191 mm.). Such stents are known and disclosed, for example, in Pinchuk, U.S. Pat. No. 5,019,090, assigned to the assignee of the present invention and incorporated herein in its entirety by reference. A suitable stent is the Cordis peripheral balloon expandable stent available from Cordis Corporation, Miami Lakes, Fla.

The delivery assembly includes the balloon catheter 16 and the introducer 20. Suitable catheters include the Opta 5 and the Power Flex Cordis PTA catheters available from Cordis Corporation, Miami Lakes, Fla. A suitable introducer is also available from Cordis Corporation. In the preferred embodiment, expansion of the stent 12 to a desired expanded diameter is achieved by inflation of the catheter balloon portion 32 on which the stent has been crimped. It will be appreciated, however, that a stent expandable by alternate methods, such as self-expanding stents and thermally expanding stents, is within the scope of the present invention.

The stent cover 14 is comprised of a tubular shaped length of a single ply or layer of woven polyester. The cover 14 is cut from a single ply sleeve or tube of woven polyester fabric. Preferably, the sleeve (and therefore the cover 14) has a thickness of approximately 0.004 inches (0.102 mm.). The preferred polyester is polyethylene terephthalate (PET). The stent cover 14 is cut from the woven sleeve to a length just slightly less than a length of the selected stent the cover will be used with. That is, end portions 34a, 34b of the stent 12 extend beyond ends of the stent cover 14. The inner diameter of the cover 14 must be at least as large as the outer diameter of the stent when the stent is expanded to its desired outer diameter within the blood vessel 26. As noted above, the stent 12 has a range of outer diameters. For example, assuming the stent 12 has a range of expanded outer diameters ranging from 0.157 in. to 0.276 in. (4.0 mm to 7.0 mm.) and it is desired that the stent 12 be expanded to an outer diameter of 0.197 in. (5.0 mm.) in the blood vessel 26, the endoprosthesis assembly 10 would be crimped to the balloon portion 32 of a balloon catheter 12 having an outer diameter of 0.197 in. (5.0 mm.) when the balloon portion is fully inflated. Similarly, the stent cover 14 must be fabricated to have an inner diameter of at least 0.197 in. (5.0 mm.). More generally, the stent cover 14 would be fabricated to have an open or unwrapped inner diameter which matches maximum expanded outer diameter of the size stent to be used. For example, if the stent 12 had a maximum outer diameter of 0.276 in. (7 mm.), then, the stent cover 14 would be required to have inner diameter of 0.276 in. (7 mm.) to be able to be used with the stent in its maximum expanded configuration. If the stent 12 is expanded to an outer diameter less than its maximum outer diameter, the stent cover 14 will have small folds pressed against the blood vessel intraluminal wall. If this occurs, however, the cover 14 will still function as intended.

A complete discussion of the weaving of PET polyester for use as a vascular prosthesis for arterial replacement may be found in Chapter 8 of *Biocompatability of Clinical Inplant Materials*, Volume II, Chapter 8, pages 178–205, CRC Series in Biocompatability, David F. Williams, Editor, CRC Press, Inc., Boca Raton, Fla. Chapter 8 is entitled "Polyethylene Terephthalate (Dacron ®) Vascular Prosthesis—Material and Fabric Construction Aspects" and is written by M. King, P. Blais, R. Guidoin, E. Prowse, M. Marcois, C. Gosselin and H. P. Noel. The foregoing publication is incorporated herein in its entirety by reference. It should be appreciated, however, that other yarns besides PET polyester are suitable for constructing the stent cover 14 including polytetrafluoroethylene (PTFE) and polypropylene. Moreover, in addition to weaving, the stent cover 14 may be fabricated by knitting and braiding techniques known to those skilled in the art.

As noted above, the stent cover 14 is cut to a length just shorter than an unexpanded length of the stent 12 . A heated anvil is used to cauterize the ends of the cover 14 after being cut to avoid fraying the weave. As typical examples, the following stent and cover lengths are suitable:

| STENT LENGTH | | COVER LENGTH | |
|---|---|---|---|
| (inches) | (cm.) | (inches) | (cm.) |
| 1.18 | 3.0 | 1.10 | 2.8 |
| 1.97 | 5.0 | 1.80 | 4.8 |

The cover 14 is slid over the unexpanded stent 12 as shown in FIG. 2 such that the cover is located equidistant from the stent end portions 34a, 34b. Since the inner diameter of the cover 14 is greater than the unexpanded outer diameter of the stent 12, there is a length of the cover labeled L in FIG. 2 that extends away from the stent when the cover is positioned around the circumference of the stent. A single suture (not shown) is wrapped around a junction of two support members 40 near the distal end 34a of the stent 12 and stitched through a single layer of the cover 14 near its distal end to secure the cover 14 to the stent. A triple knot is then tied on an outer surface of the cover 14. A suitable suture material is 5–0 Prolene available from Ethicon of Somerville, N.J.

Holding a portion of the cover 14 labeled P (FIG. 2) firmly against the stent, the length L is wrapped or folded back on itself in the direction labeled W as tightly as possible, resulting in the wrapped configuration shown in FIG. 3. In the wrapped configuration of the cover 14, doubled ends 42 of the cover nearly touch, the ends being spaced apart by a single layer of the cover (approximately 0.004 inches (0.102 mm.)). Except for the single layer portion of the wrapped cover 14 extending between the doubled ends 42, the wrapped cover is three layers thick. Of course it should be understood that a stent having a ratio of desired expanded outer diameter to unexpanded outer diameter other than three will result in a different wrapped cover configuration than the three layer thick configuration shown in the drawings.

After the stent cover 14 is wrapped around the stent 10, the assembly 10 is inserted into a section of heat shrink tubing 44 (FIG. 4) having an inner diameter just slightly larger than an unexpanded outer diameter of the assembly 10. For a stent 12 having a range of outer diameters from 0.157 in. to 0.276 in. (4.0 mm. to 7.0 mm.) and a desired expanded outer diameter of 0.197 in. (5.0 mm.), the outer diameter of the assembly 10, in its unexpanded configuration is approximately 0.08 in. (1.97 mm.) and a section of heat shrink tubing is used having an inner diameter corresponding to the outer diameter of the assembly, that is, approximately 0.08 in. (1.97 mm.). The assembly 10 and the heat shrink tubing 44 are placed in an oven at 220° C. for five minutes. The heat of the oven thermally sets the cover 14 in its wrapped configuration. The assembly 10 and the heat shrunken tubing 44 are then removed from the oven and the tubing is stripped off. Appropriate heat shrink tubing may be obtained from Advanced Polymers, Inc. of Salem, N.H.

The completed assembly 10 is inserted over the PTA balloon catheter 16 which includes the balloon portion 32 expandable to the desired outer expanded diameter of the stent 12, namely, 0.197 in. (5.0 mm.). The stent 12 is crimped onto the balloon portion 32 using a crimping tool of conventional design. The endoprosthesis assembly 10, which is expandable to outer diameter of 0.197 inches (5 mm.), can be passed through a size 7 French introducer. If the endoprosthesis assembly of the present invention includes a stent 12 with a range of outer diameters of 0.314 in. to 0.472 in. (8 mm. to 12 mm.) and has a desired expanded outer diameter of 0.315 inches (8 mm.) and is mounted on a catheter with a balloon portion expandable to 0.315 in. (8 mm.), the assembly can be passed through a size 8 French introducer. If the endoprosthesis assembly of the present invention includes a stent with a range of outer diameters of 0.314 in. to 0.472 in. (8 mm. to 12 mm.) and has a desired expanded outer diameter 0.472 inches (12 mm.) and is mounted on a catheter with a balloon portion expandable to 0.472 in. (12 mm.) the assembly can be passed through a size 8 French introducer.

The following table summarizes dimensions of typical endoprosthesis assemblies of the present invention for three desired stent expanded sizes and corresponding required introducer passageway inner diameters:

| INTRODUCER PASSAGEWAY I.D. | | ASSEMBLY O.D. (expanded stent) | | ASSEMBLY O.D. (stent unexpanded) | |
|---|---|---|---|---|---|
| (French) | (mm.) | (inches) | (mm.) | (inches) | (mm.) |
| 7 | 2.33 | .97 | 5.0 | .078 | 3.0 |
| 8 | 2.67 | .315 | 8.0 | .100 | 2.5 |
| 9 | 3.00 | .472 | 12.0 | .115 | 3.0 |

Conventional endoprosthesis assemblies comprising a stent and a cover require the use of a size 9 French introducer for a 5.0 mm. expanded stent assembly and a size 12 French introducer for a 8.0 mm expanded stent assembly. The reduction in the required introducer size achieved by the present invention is of particular significance, since a smaller incision reduces the risk that surgical closure of the entrance incision will be required. General rule is that incisions for size 20 French and larger introducers require surgical closure. The reduction in the required introducer size also reduces the risk of developing hematomas and other bleeding complications.

It is of particular significance in the present invention that the unwrapped inner diameter of the cover 14 is matched to the maximum expanded outer diameter of the stent 12. With this configuration, the cover 14 in its unwrapped or released condition not exert an inward radial force on the expanded stent 12 which would tend to cause the expanded stent to collapse. The stent 12 is matched to the catheter 16 such that the length of the stent is less than a length of the balloon portion 32. As can best be seen in FIG. 9, the stent 12 is positioned and crimped on the balloon 32 to avoid the ends of the balloon 32 that taper to a sealed connection with the catheter 16 upon inflation.

As can be seen in FIGS. 7 and 10, an exterior surface of the cover 14 engages an interior surface of the occluded material 28. The cover 14 is compliant after opening enabling it to conform around the support members 40 of the expanded stent 14, thereby creating an undulating outer surface of the assembly 10 which is implanted into the exposed surface of the occluded material 28. This undulating outer surface of the expanded cover 14 increases the contact surface area between the occluded material 28 and the cover and reduces the potential for migration of the assembly. The weave of the cover 14 has limited porosity permitting beneficial cellular ingrowth while preventing malignant growth into the interior region of the expanded stent 12. While the preferred embodiment contemplates an assembly for deployment within the vasculature, it will be appreciated that the invention can be used to reinforce or restore the patency of other body passageways, such as the esophagus and trachea.

While the present invention has been described with a degree of particularity, it is the intent that the invention include all modifications and alterations from the disclosed design falling within the spirit and scope of the appended claims.

What is claimed is:

1. A method of fabricating an endoprosthesis assembly for percutaneous deployment and implantation at a treatment site within a patient's body, the steps of the method comprising:

a) providing a cylindrically shaped stent expandable from a first configuration to a second enlarged configuration;

b) inserting the stent in its first configuration into a cylindrical stent cover having a length less than a length of the stent and having an inner diameter at least as large as an outer diameter of the stent when the stent is in its second enlarged configuration;

c) affixing the stent cover to the stent;

d) wrapping the stent cover around the stent, the stent cover in its wrapped configuration having a substantially uniform cross sectional area over an entire length of the stent cover;

e) releasably setting the stent cover in its wrapped configuration for deployment of the assembly to the treatment site; and f) releasably affixing the assembly to an expandable portion of a delivery catheter for deployment of the assembly to the treatment site.

2. The method of fabricating an endoprosthesis assembly set forth in claim 1 wherein the step of releasably setting the stent cover in its wrapped configuration includes the substeps of:

i) inserting the stent and wrapped stent cover in a central opening of a section of heat shrink tubing;

ii) heating the stent, wrapped stent cover and heat shrink tubing to thermally set the stent cover in its wrapped configuration; and iii) stripping the heat shrink tubing off the cover.

3. The method of fabricating an endoprosthesis assembly set forth in claim 1 wherein the step of releasably affixing the assembly to the expandable portion of the delivery catheter includes crimping the stent to the delivery catheter expandable portion.

4. A method of percutaneously deploying and implanting an endoprosthesis assembly including a stent and stent cover affixed to the stent at a treatment site within a patient's body, the stent being cylindrically shaped and radially expandable from a first configuration to a second enlarged configuration and the stent cover being cylindrically shaped and having a length less than a length of the stent and an inner diameter at least as large as an outer diameter of the stent when the stent is in its second enlarged configuration, the steps of the method comprising:

a) wrapping the stent cover around an outer surface of the stent, the stent cover in its wrapped configuration having a substantially uniform cross sectional area over an entire length of the stent cover;

b) releasably setting the stent cover in its wrapped configuration for deployment of the assembly to the treatment site; and c) releasably affixing the assembly to an inflatable portion of a delivery catheter for deployment of the assembly to the treatment site;

d) inserting an end of the catheter into the patient's body through an introducer and advancing the catheter into the body until the assembly is adjacent the treatment site;

e) inflating the inflatable portion of the delivery catheter to implant the assembly, the inflation of the inflatable portion detaching the assembly from the expandable portion, radially expanding the stent to its second expanded configuration, and at least partially unwrapping the stent cover such that the cover conforms to the outer surface of the stent when the stent is in its second expanded configuration.

5. The method of percutaneously deploying and implanting an endoprosthesis assembly set forth in claim 4 wherein the step of releasably setting the stent cover in its wrapped configuration includes the substeps of:

i) inserting the stent and wrapped stent cover in a central opening of a section of heat shrink tubing;

ii) heating the stent, wrapped stent cover and heat shrink tubing to thermally set the stent cover in its wrapped configuration; and iii) stripping the heat shrink tubing off the cover.

6. The method of fabricating an endoprosthesis assembly set forth in claim 4 wherein the step of releasably affixing the assembly to the expandable portion of the delivery catheter includes crimping the stent to the delivery catheter expandable portion.

* * * * *